(12) United States Patent
St. Cyr et al.

(10) Patent No.: US 6,429,198 B1
(45) Date of Patent: Aug. 6, 2002

(54) COMPOSITIONS FOR INCREASING ATHLETIC PERFORMANCE IN MAMMALS

(75) Inventors: John St. Cyr, Coon Rapids; Clarence A. Johnson; Scott Hagerman, both of Wyoming, all of MN (US); Louis W. Vasquez, Denver, CO (US); Terri L. Butler, Minneapolis, MN (US)

(73) Assignee: Bioenergy Inc., Ham Lake, MN (US)

( * ) Notice: Subject to any disclaimer, the term of this patent is extended or adjusted under 35 U.S.C. 154(b) by 0 days.

(21) Appl. No.: 09/677,639

(22) Filed: Oct. 3, 2000

Related U.S. Application Data (63) Continuation-in-part of application No. 09/290,789, filed on Apr. 12, 1999, now Pat. No. 6,159,942.

(51) Int. Cl.$^7$ .............................................. A61K 31/70
(52) U.S. Cl. ........................................................ 514/23
(58) Field of Search ........................................... 514/23

(56) References Cited

U.S. PATENT DOCUMENTS

| | | | |
|---|---|---|---|
| 4,228,215 A | 10/1980 | Hein, III et al. | 428/216 |
| 4,871,718 A | 10/1989 | Carniglia | 514/23 |
| 4,968,719 A | 11/1990 | Brevetti | 514/556 |
| 5,292,538 A | 3/1994 | Paul et al. | 426/74 |
| 5,391,550 A | 2/1995 | Carniglia et al. | 514/23 |
| 5,707,971 A | 1/1998 | Fahy | 514/43 |
| 5,709,971 A | 1/1998 | Bowman et al. | 430/14 |
| 5,714,515 A | 2/1998 | Bunger | 514/557 |
| 5,804,596 A | 9/1998 | Majeed et al. | 514/455 |
| 6,051,236 A | 4/2000 | Portman | 424/195.1 |

FOREIGN PATENT DOCUMENTS

| | | | |
|---|---|---|---|
| DE | 4228215 A1 | 3/1994 | A61K/31/70 |
| EP | 0312249 | 4/1989 | A61K/33/08 |
| EP | 0573466 | 12/1993 | A61K/31/70 |
| EP | 0680945 | 11/1995 | C07C/229/22 |
| WO | 94/02127 | 2/1994 | A61K/31/195 |
| WO | 96/18313 | 6/1996 | A23L/1/305 |

OTHER PUBLICATIONS

Gross, M., et al., "Metabolism of D–Ribose Administered Continuously to Healthy Persons and to Patients with Myoadenylate Deaminase Deficiency", *Klin Wochenschr*, 67, pp. 1205–1213, (1989).

Gross, M., et al., "Ribose adminstration during exercise: effects on substrates and products of energy metabolism in healty subjects and a patient with myoadenylate deaminase deficiency", *Klin. Wochenshr.*, 69, pp. 151–155, (1991).

Pliml, W., et al., "Effects of ribose on exercise–induced ischaemia in stable coronary artery disease", *The Lancet*, 340, pp. 507–510, (Aug. 29, 1992).

Tullson, P.C., et al., "Adenine nucleotide Syntheses in Exercising and Endurance–trained Skeletal Muscle", *The American Journal of Physiology*, 261 (2), pp. C342–C347, (1991).

Tullson, P.C., et al., "IMP Metabolism in Human Skeletal Muscle After Exhaustive Exercise", *The American Journal of Physiology*, pp. 146–152, (1995).

Zimmer, H.G., et al., "Ribose accelerates the repletion of the ATP pool during recovery from reversible ischemia of the rat myocardium", *Journal of Molecular and Cellular Cardiology*, 16 (9), pp. 863–866, (Sep. 1984).

Zollner, N., et al., "Myoadenylate Deaminase Deficiency: Successful Symptomatic Therapy by High Dose Oral Administration of Ribose", *Klin Wochenschr*, 64, pp. 1281–1290, (1986).

*Primary Examiner*—James H. Reamer
(74) *Attorney, Agent, or Firm*—Schwegman, Lundberg, Woessner & Kluth, P.A.

(57) ABSTRACT

Pentose is administered to mammals to increase athletic performance and reduce fatigue.

17 Claims, 6 Drawing Sheets

MEAN POWER PER SPRINT SESSION. CALCULATED AS AN AVERAGE OF THE MEAN POWER OF 15 SPRINTS DURING EACH SPRINT SESSION

COMPOSITIONS FOR INCREASING ATHLETIC PERFORMANCE IN MAMMALS

FIELD OF THE INVENTION

This application is a Continuation-in-part of application Ser. No. 09/290,789, filed on Apr. 12, 1999, now U.S. Pat. No. 6,159,942.

The present invention relates to compositions and methods for increasing the athletic performance of mammals. Administration of the compositions of the invention provides increased power output and reduced fatigue.

BACKGROUND OF THE INVENTION

It is well known that the energy coinage of the cell is adenosine triphosphate (ATP). During anabolism, the energy derived from the metabolism of nutrients is transferred to high energy phosphate bonds of ATP. The energy in these bonds is expended during the energy consumption phase. An important and "costly" expenditure, in which ATP is rapidly cycled, is that required for muscular contraction.

The energy buildup steps occur within the muscle cell during two basic processes. Oxidative phosphorylation replenishes ATP by the breakdown of circulating fatty acids, glucose and intramuscular glycogen and triglycerides. Anaerobic phosphorylation provides ATP from creatine phosphate, circulating glucose and intramuscular glycogen via kinase reactions such as the myokinase reaction.

U.S. Pat. No. 5,714,515 describes the administration of compositions containing pyruvate, an intermediate breakdown product of glucose, to enhance recovery from surgical or accidental trauma, shock, exhaustion due to prolonged physical effort and other indications. U.S. Pat. No. 5,709,971 discloses the administration of other glucose metabolites, namely glyceraldehyde-3-phosphate, phosphoenolpyruvate and 3-phosphoglycerate, in combination with nicotineadeninedinucleotide, coenzyme A and acetyl coenzyme A.

A different approach to increasing the substrates available for production of ATP that has been employed is the administration of the amino acid L-carnitine, which is thought to enhance the transport and absorption of fatty acids into mitochondria, the site of oxidative phosphorylation. U.S. Pat. No. 4,968,719 describes the use of L-carnitine for the treatment of peripheral vascular diseases.

Regardless of whether the high energy phosphate bonds of ATP are generated oxidatively or anaerobically, and irrespective of the substrates used for its generation, ATP cannot be synthesized unless the precursors of the ATP molecule itself are available. The synthesis of the ATP molecule can occur by de novo or salvage pathways.

In the synthesis of ATP via the nucleotide salvage pathway, the nucleotide precursors that may be present in the tissue are converted to AMP and further phosphorylated to ATP. Adenosine is directly phosphorylated to AMP, while xanthine and inosine are first ribosylated by 5-phosphorihosyl-1-pyrophosphate (PRPP) and then converted to AMP. Ribose is found in the normal diet only in very low amounts, and is synthesized within the body by the pentose phosphate pathway. In the de novo synthetic pathway, ribose is phosphorylated to PRPP, and condensed with adenine to form the intermediate adenosine monophosphate (AMP). AMP is further phosphorylated via high energy bonds to form adenosine diphosphate (ADP) and ATP.

Synthesis by the de novo pathway is slow. Normally, AMP synthesis is believed to occur mainly by the salvage pathway, however, following anoxia or ischemia, the activity of the de novo pathway is increased.

During energy consumption, ATP loses one high energy bond to form ADP, which can be hydrolyzed to AMP. AMP and its metabolites adenine, hypoxanthine and inosine are freely diffusible from the muscle cell and may not be available for resynthesis to ATP via the salvage pathway.

In U.S. Pat. No. 4,719,201, it is disclosed that when ATP is hydrolyzed to AMP in cardiac muscle during ischemia, the AMP is further metabolized to adenosine, inosine and hypoxanthine, which are lost from the cell upon reperfusion. In the absence of AMP, rephosphorylation to ADP and ATP cannot take place. Since the precursors were washed from the cell, the nucleotide salvage pathway is not available to replenish ATP levels. It is disclosed that when ribose is administered via intravenous perfusion into a heart recovering from ischemia, recovery of ATP levels is enhanced.

Pliml, in German Patent No. 4,228,215, discloses that oral ribose was effective in treating cardiac insufficiency and hypovolemic shock in humans.

The advantage of the administration of pentoses such as ribose or xylitol to prevent pain and stiffness of skeletal muscle in patients suffering from the autosomal recessive genetic disease myoadenylate deaminase (MAD) deficiency was shown by Zöllner et al. (Klinische Wochenshritt 64: 1281–1290, 1986.) This disease is characterized by permanent muscular hypotonia, excessive muscular weakness, fatigue, soreness, burning pain, stiffness and cramps. These symptoms are considered to be consequences of the interruption of the ATP cycle. Dephosphorylation of ATP is inhibited by the accumulation of AMP, resulting in less available energy to effect muscle contraction and relaxation. However, even though symptoms of MAD-deficient patients were relieved by administration of ribose, the intracellular levels of adenine nucleotides remained abnormally high and normal volunteers experienced no beneficial effect from ribose administration. (Gross, Reiter and Zöllner, Klinische Wochenshritt, 67:1205–1213, 1989.)

Tullson et al. (Am. J. Physiol., 261 (Cell Physiol. 30) C343–347, 1991) cite references showing that high intensity exercise increases degradation and subsequent loss of AMP from isolated muscle. They further disclose that adding ribose to the perfusate in a rat hindquarter preparation increases the de novo synthesis of AMP in sedentary muscle, but does not eliminate the decline in de novo synthesis seen in contracting muscle.

Camiglia, et al, U.S. Pat. No. 4,871,718, disclose th at when a complex mixture comprising amino acids, metabolites, electrolytes and ribose or a precursor of ribose, was administered orally as a dietary supplement to race horses, increases in intracellular ATP levels and physical performance result. The performance evaluation was anecdotal, based on the subject's performance history. When the composition of the components of the supplement is calculated, it is found that the daily supplementation contains 100–200 g protein, 75–150 g simple carbohydrates and only 2-4 g ribose, an insignificant amount in terms of physiological effect on a mammal weighing approximately 1000 pounds.

Thus, a continuing need exists for simple and effective methods to enhance athletic performance in mammals.

SUMMARY OF THE INVENTION

The present invention provides compositions and methods of increasing the athletic performance in a mammal such as a human or equine athlete. Specifically, a pentose such as D-ribose is given orally before, during and/or after a period of exercise, in amounts effective to increase the athletic performance of the mammal. Mammals given pentose as a nutritional supplement are able to exercise longer, i.e., to achieve and maintain a higher intensity of physical activity with reduced fatigue, than those not given ribose. Preferably, the pentose is taken at a time such that circulating levels of the administered pentose are available to coincide with high energy demands, that is, before, during and after the exercise. More preferably, pentose is taken daily whether or not the mammal is exercising strenuously. More preferably, ribose is taken in combination with other nutritional supplements, most preferably with creatine.

Nutritional supplements that enhance the pentose benefit are also provided. Such compositions preferably comprise at least one of magnesium ($Mg^{+2}$), creatine, pyruvate, L-carnitine, stimulants, energy pathways intermediates and optionally at least one vasodilating substance. Of these, creatine is most preferred in combination with ribose, Mammals undergoing high energy demand and loss of fluids also benefit from a composition that further comprises electrolytes and an additional energy source such as carbohydrate.

DETAILED DESCRIPTION OF THE INVENTION

The present invention provides a method of increasing athletic performance by the oral administration of a pentose and provides pentose-containing compositions that are especially beneficial to mammals exercising to a state of fatigue.

It has already been shown in Applicants' co-pending patent application Ser. No. 09/290,789, now U.S. Pat. No. 6,159,942 that not only does pentose administration benefit sick mammals, that is, those who have experienced an acute or chronic ischemic insult or that have a metabolic disease, but that healthy mammals can increase their energy levels by the administration of ribose, as reflected in higher concentrations of ATP in muscle biopsies. However, increase in energy level does not automatically result in an increase in athletic performance. Improvements in athletic performance must include objective increases in speed, strength, endurance and the like. For performance involving more than short efforts that are not extremely intensive or repeated several times, recovery from fatigue is a crucial parameter of performance.

Foremost among agents that are known to increase athletic performance are anabolic steroids, erythropoietin, blood doping and growth hormone. Most of these agents have severe side effects and are banned in athletic competition.

While raising the energy levels, as shown in the '789 application, is beneficial to the non-athlete or casual exerciser, in order to optimize the physiological processes that result in improved athletic performance, it is desirable to combine the main enhancer, pentose, with compositions directed to stimulating each pathway. Many agents are known to raise energy levels but may not increase athletic performance. Included among such agents are stimulants such as ephedrine and ginseng. The stimulant caffeine raises energy and may have some effect on performance. Forskohlin is a plant extract known to affect cyclic AMP, providing a stimulation effect as is more fully explained in U.S. Pat. No. 5,804,596. While marginally effective alone in increasing athletic performance, stimulants may enhance the pentose effect.

Energy ultimately is derived from the oxidation of sugars, fatty acids and protein. Tricarboxylic acid cycle intermediates and glycolysis intermediates such as pyruvate add a "pre-processed" fuel to the major aerobic energy-yielding pathways. By entering a energy-yielding pathway at a point past the initiation point, intervening enzymatic steps are bypassed, leading to stimulation of energy production. Carnitine, an amino acid that adds in delivery of fatty acid molecules to the mitochondria for use as fuel, is widely used by athletes to speed up fat metabolism by enhancing fat transport.

Proteins and amino acids such as glutamine and arginine are important factors as fuel, but more especially act to hasten cellular growth and repair, especially of muscle. Glutamine and arginine also have a vasodilating effect. Protein is best provided as whey protein, soy protein, egg albumin or casein, all of which are economical and easily digested. U.S. Pat. No. 6,051,236 discloses a nutritional compound in a dry powder form comprising protein, amino acids, carbohydrates and vitamins C and E. The composition increases muscle performance during exercise and enhances muscle cell repair and recovery following the cessation of exercise.

Undoubtedly, the most important factor in increasing athletic performance is athletic training. It has been known literally for millennia that the best athlete is the one who works the hardest at increasing performance. During training, all the myriad processes that contribute to athletic performance are gradually stepped up toward physiological optimization.

The conditioned athlete also will have optimized his or her general health by a proper diet that provides the optimal levels of protein, carbohydrates, vitamins and minerals. However, it may be convenient to further supplement the diet at the same time as pentose is administered.

Since each of the following groups of compounds affect different pathways that add to the totality of athletic performance, it is expected that the addition of any one will enhance the pentose effect on athletic performance.

| | |
|---|---|
| Group 1. | Supplements contributing to general health and nutrition:<br>vitamins<br>minerals<br>proteins and amino acids<br>carbohydrates<br>essential fatty acids |
| Group 2. | Stimulants:<br>caffeine<br>ephedrine<br>forskholin |

-continued

| Group 3. | Energy pathway substrates and intermediates:<br>carbohydrates<br>proteins and amino acids<br>tricarboxylic cycle intermediates<br>free fatty acids<br>pyruvate |
|---|---|
| Group 4. | Vasodilators:<br>arginine<br>glutamine |
| Group 5. | Others:<br>creatine<br>carnitine<br>ipriflavone |

For the purpose of describing this invention, the following terms have the following meanings:

1. "Pentose" means a monosaccharide, including but not limited to, ribose, D-ribose, ribulose, xylitol, xylulose, and any 5-carbon precursor of ribose.

2. "Athletic performance" means strong, precise, controlled movements that can be maintained over the time desired by an athlete to achieve a particular result of strength, speed, power and/or precision. "Athlete" is here defined as a mammal who performs such movements, either in competition or for recreation. Athletes include cyclists, swimmers, bodybuilders, racehorses, racing dogs and the like. An increase in athletic performance is measured as higher power output, more stamina, or faster speed, preferably in combination with precision of movement or an increase in frequency of performance or movements.

3. "Fatigue" means the inability to maintain a consistent level of peak athletic performance for a desired period of time. Fatigue is this definition is here defined to be due to the exhaustion of energy sources to metabolize; buildup of toxic metabolites in muscle and the like; but not due to lack of sleep, metabolic disease or illness.

Pentose can be given alone or in combination with a substance selected from one or more of groups 1 to 5 above, all of which can give an incremental improvement in benefit, particularly those which act in a complementary, but different, manner. For example, creatine, when phosphorylated, acts as an energy "reservoir" in muscle, in that it can readily transfer a high-energy phosphate bond to ADP to form ATP. Intermediates of the glycolytic pathways may drive the pathway to greater activity by bypassing "slow" enzymatic steps, with resulting greater synthesis of high-energy bonds. Carnitine increases the delivery of fat to the mitochondria, where it is metabolized for energy.

The compositions preferably contain a performance-enhancing amount of pentose dissolved or dispersed in an aqueous vehicle such as water, that may optionally contain minor but effective amounts of additives such as polyols, preservatives, flavorings, colorings and the like. Compositions containing pentoses adapted for oral administration also include solid dosage forms such as tablets, lozenges, capsules and the like. Pentoses may also be incorporated in solid nutriments such as bars, moist or dry animal food, powders or drink mixes. Effective total dosages of ribose, which can be extrapolated to other pentoses, are disclosed hereinbelow.

Because pentoses are naturally occurring sugars with a pleasant taste and virtually no toxicity, subjects may be encouraged to self-administer pentose as a nutritional supplement in the form of tablets, lozenges, powders, suspensions, solutions, or mixed in with solid or liquid food.

When the subject is canine or feline, pentose can be easily integrated into "senior diet" or "cardiac diet" and separate administration is not necessary. When the subject is human, pentose can be included in drinks, bars, shakes or snack food. When the subject is equine, pentose can be mixed in with feed or given in water. The preferred pentose is ribose or xylitol. The preferred dosage is 0.1 to 200 gm pentose per day, preferably 1 to 20 gm pentose per day for a human athlete and 30-150 g per day for a horse. An average adult human may find that 4 to 8 gm pentose per day is sufficient to provide the benefits of the invention. The upper dose is limited only by the taste preference of the subject, although at very high doses, subjects may experience diarrhea. The dose may be given once a day in a single unit dosage form, but preferably is given two or three times throughout the day, most conveniently before and/or during and/or following exercise.

During strenuous activity, humans and horses may sweat profusely, requiring replacement of body fluids and electrolytes. Subjects such as dogs, which do not sweat, lose copious amount of water through the lungs and also require fluid replacement. In addition to the advantages provided by pentoses alone, with carnitine and or vasodilating agents, it is convenient to include other components within a replacement solution to be drunk during and following exercise. Rehydration solutions such as Gatorade®, Thirst Quencher, and Max® drinks are among those popular with athletes.

These sustained energy and anabolic formulas are generally made up of different carbohydrates, including corn syrup, sucrose, fructose, and maltodextrin; proteins, including casein and other proteins from milk and soybean; and lipids, including corn, soy, safflower, and canola oils and medium chain triglycerides.

U.S. Pat. No. 5,292,538 describes an energy sustaining composition containing fructose, glucose, hydrolyzed protein and magnesium complexed by an amino acid chelator. Other ingredients noted as especially advantageous include potassium, phosphorus, manganese, zinc, boron, copper, molybdenum, chromium, vanadium, vitamins $B_{1,2,5,6}$ and $B_{12}$, C, E and carnitine.

U.S. Pat. No. 5,114,723 describes hypotonic beverage compositions for oral administration comprising electrolytes, minerals, carbohydrates and other ingredients. The compositions are adjusted to have an osmolarity between 100 and 270 mOs/l.

Each of these rehydration drinks can be improved by the addition of from about 1 to 20% pentose, most preferably 10% by weight to volume. The amount of pentose to be added will depend on the composition of other nutrients, to keep the osmolarity within the preferred limits. These drinks will be further improved by the addition of other energy metabolites and co-factors.

The invention will be further described by reference to the following examples.

EXAMPLE 1

Effect of D-ribose On Nucleotide Salvage in Resting Rat Muscle.

It has been theorized but not objectively shown that ribose, via PRPP synthesis, increases the rate of ATP synthesis via the nucleotide salvage pathway. However, nothing is known about the total adenine nucleotide (TAN) or ribose levels in the resting muscle and therefore, it is possible that the synthetic enzyme pathway is already saturated and that administration of ribose does not increase ATP levels in normal, non-ischemic skeletal muscle. In order to demonstrate the effect of ribose on the pathway, plantaris complex muscles of healthy adult male Sprague-Dawley rats were surgically exposed and perfused with reconstituted blood perfusion medium containing amino acids, mM glucose and 100 μU of bovine insulin/ml. The muscle was perfused with reconstituted blood medium at ~40 ml/min, providing tissue perfusion of approximately 0.65 ml/min. Varying concentrations of D-ribose were added to the perfusate to bring the concentration to 0.156 mM, 0.5 mM, 1.58 mM, 5.0 mM and 15.0 mM. The muscle was perfused for 30 minutes. A minimum of two rats was used for analysis at each dose of ribose tested.

Following perfusion, muscle sections were quickly dissected from the limb and freeze-clamped with aluminum tongs chilled in liquid nitrogen. Muscle sections were lyophilized and reconstituted in distilled water for subsequent separation of adenine nucleotides by reverse-phase high pressure liquid chromatography. Results are expressed as salvage of adenine (i.e., formation of ATP) in nanomoles salvaged per gram wet weight of muscle per hour (nM/gm/hr).

TABLE I

Ribose Skeletal Muscle Dose-Response Kinetics

| mM Ribose | Observed | Saturation Kinetics with Base |
|---|---|---|
| 0.000 | 48.6 | |
| 0.158 | 113.0 | 85.82 |
| 0.500 | 110.0 | 118.68 |
| 1.000 | | 154.12 |
| 1.580 | 188.5 | 183.51 |
| 2.000 | | 199.74 |
| 2.500 | | 215.29 |
| 3.000 | | 227.85 |
| 5.000 | 250.0 | 260.68 |
| 15.000 | 315.5 | 310.37 |

Figure 1:
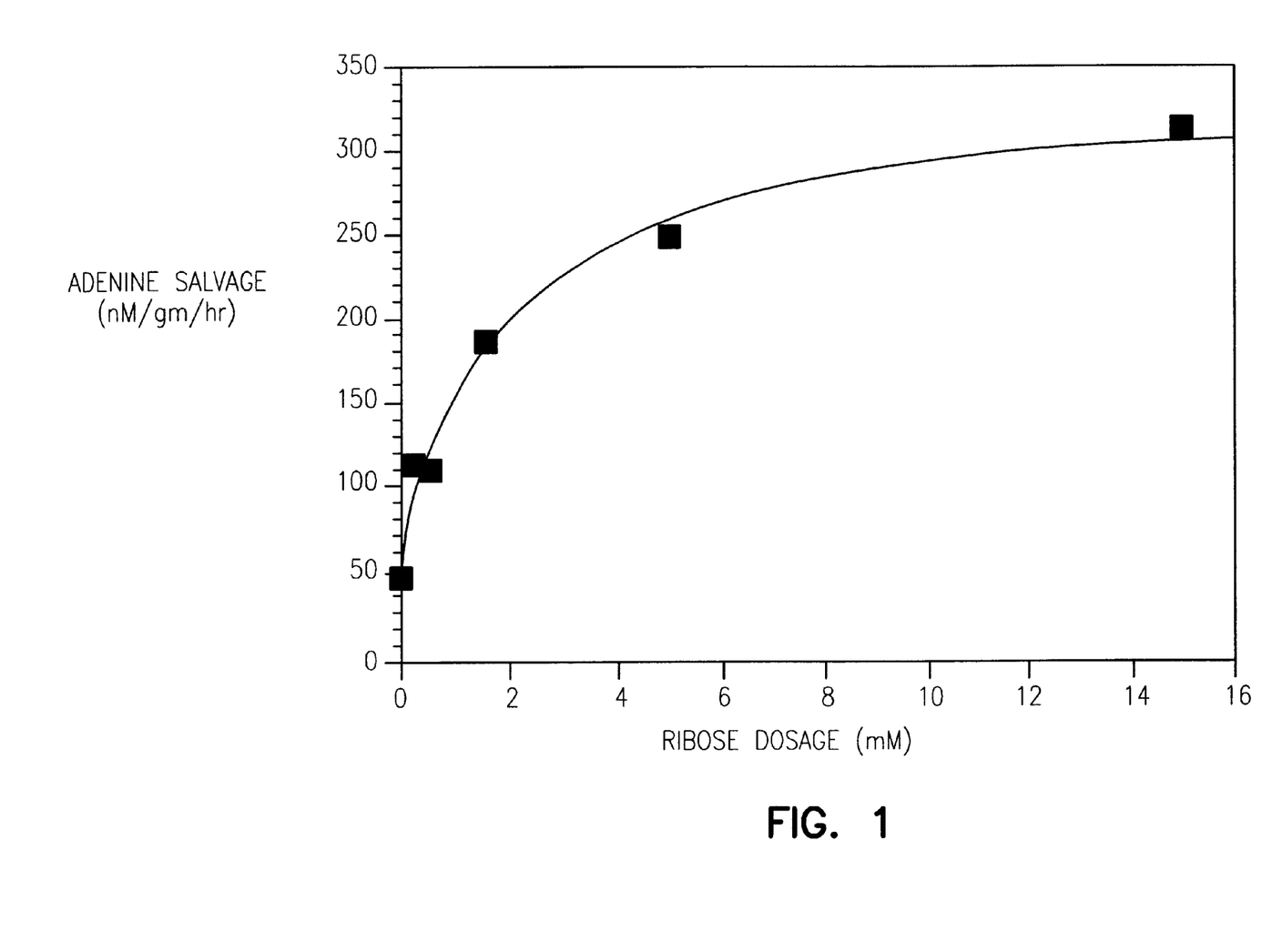
FIG. 1 shows the dose response of the adenine salvage pathway in normal adult rats to the administration of ribose.

As is shown in FIG. 1 and Table I, adenine salvage at zero millimolar (mM) ribose is less than 50 nM/gm/hr and doubles with administration of 0.158 mM ribose. At 5 mM ribose, the rate of ATP synthesis reaches 250 nM/gm/hr. These results show that normal, healthy muscle has low baseline levels of ribose and nucleotide salvage capability, which can be increased by the administration of ribose.

EXAMPLE 2

Increased Exercise Capacity in Normal Subjects.

Four healthy, fit subjects in the age range 24 to 26 years of age were tested. The group was selected to be homogeneous regarding fitness level, gender and mean age with no known metabolic, neuronal, endocrine or cardiopulmonary disorders. All were capable of or had experience with cycling. The study protocol included four phases: (1) an initial baseline phase consisting of no exercise session; (2) a loading phase including three days of administration of either D-ribose or placebo (glucose) three times per day; (3) a training phase of three days employing exercise sessions characterized by serial (N=6) bouts of short (10 second) high-intensity cycle sprints at 7% body mass resistance with 50 second rest periods between sprints twice per day (morning and afternoon), and (4) a recovery phase for a period of 48 hours after the final training session. FIG. 1 is a diagram of a single cycle sprint bout.

Muscle biopsies (MB) were performed on the vastis lateralis muscle using both legs in order to evenly distribute and minimize sampling and possible muscle soreness per leg due to the biopsy itself The first MB was collected at rest at the beginning of the study to establish a baseline and immediately after the first training session of day 0 or the first phase. During the loading phase, no MB was taken. Muscle Biopsies were taken following the final training session and after 48 hours of recovery.

Two subjects were randomly selected for inclusion into the placebo or ribose group. Ribose or glucose was administered orally in a 250 ml iso-osmotic solution containing 10.0 grams of either ribose or placebo three times per day for three days preceding training (loading phase) and for three days during training (training phase). One-half liter isotonic electrolyte solution was given immediately post exercise and again 30 minutes later to avoid dehydration.

The concentration of the following analytes was determined in the MB samples: ATP, ADP, AMP, IMP (inosine monophosphate), TAN (total adenine nucleotides), creatine phosphate and creatine.

TABLE II

Ribose Athlete Study
Mean Power Per Kilogram (Watts)

| Subject | 1 | 2 | 3 | 4 | 5 | 6 | Average | |
|---|---|---|---|---|---|---|---|---|
| 1P | 6.0 | 6.7 | 7.3 | 7.4 | 7.3 | 7.5 | 7.0 | |
| 2R | 6.9 | 7.5 | 7.8 | 7.6 | 7.9 | 7.4 | 7.5 | |
| 3R | 8.7 | 9.2 | 9.1 | 9.0 | 8.5 | 8.2 | 8.8 | |
| 4P | 7.5 | 8.0 | 7.7 | 8.7 | 8.0 | 7.6 | 7.9 | |
| Placebo | 6.8 | 7.4 | 7.5 | 8.0 | 7.6 | 7.5 | 7.5 | 100.0% |
| Ribose | 7.8 | 8.4 | 8.5 | 8.3 | 8.2 | 7.8 | 8.2 | 109.0% |

TABLE III

Ribose Athlete Study
Peak Power Per Kilogram (Watts)

| Subject | 1 | 2 | 3 | 4 | 5 | 6 | Average | |
|---|---|---|---|---|---|---|---|---|
| 1P | 6.8 | 7.9 | 8.6 | 8.6 | 8.3 | 9.0 | 8.2 | |
| 2R | 7.9 | 8.8 | 9.2 | 9.0 | 9.4 | 8.7 | 8.8 | |
| 3R | 9.8 | 10.6 | 10.7 | 10.7 | 10.1 | 9.9 | 10.3 | |
| 4P | 7.7 | 8.6 | 8.7 | 9.4 | 8.8 | 9.0 | 8.7 | |
| Placebo | 7.7 | 8.6 | 8.7 | 9.4 | 8.8 | 9.0 | 8.7 | 100.0% |
| Ribose | 8.9 | 9.7 | 10.0 | 9.9 | 9.8 | 9.3 | 9.6 | 109.9% |

TABLE IV

Ribose Athlete Study
Total Power Per Kilogram

| Subject | 1 | 2 | 3 | 4 | 5 | 6 | Average | |
|---|---|---|---|---|---|---|---|---|
| 1P | 59.1 | 67.0 | 72.7 | 73.3 | 72.5 | 74.2 | 69.8 | |
| 2R | 71.9 | 74.7 | 77.1 | 75.6 | 78.1 | 73.4 | 75.1 | |
| 3R | 86.8 | 91.9 | 91.3 | 90.0 | 85.4 | 82.5 | 88.0 | |
| 4P | 74.5 | 80.3 | 76.8 | 87.4 | 80.0 | 76.4 | 79.2 | |
| Placebo | 66.8 | 73.6 | 74.8 | 80.4 | 76.3 | 75.3 | 74.5 | 100.0% |
| Ribose | 79.3 | 83.3 | 84.2 | 82.8 | 81.8 | 77.9 | 81.6 | 109.5% |

Figure 2:
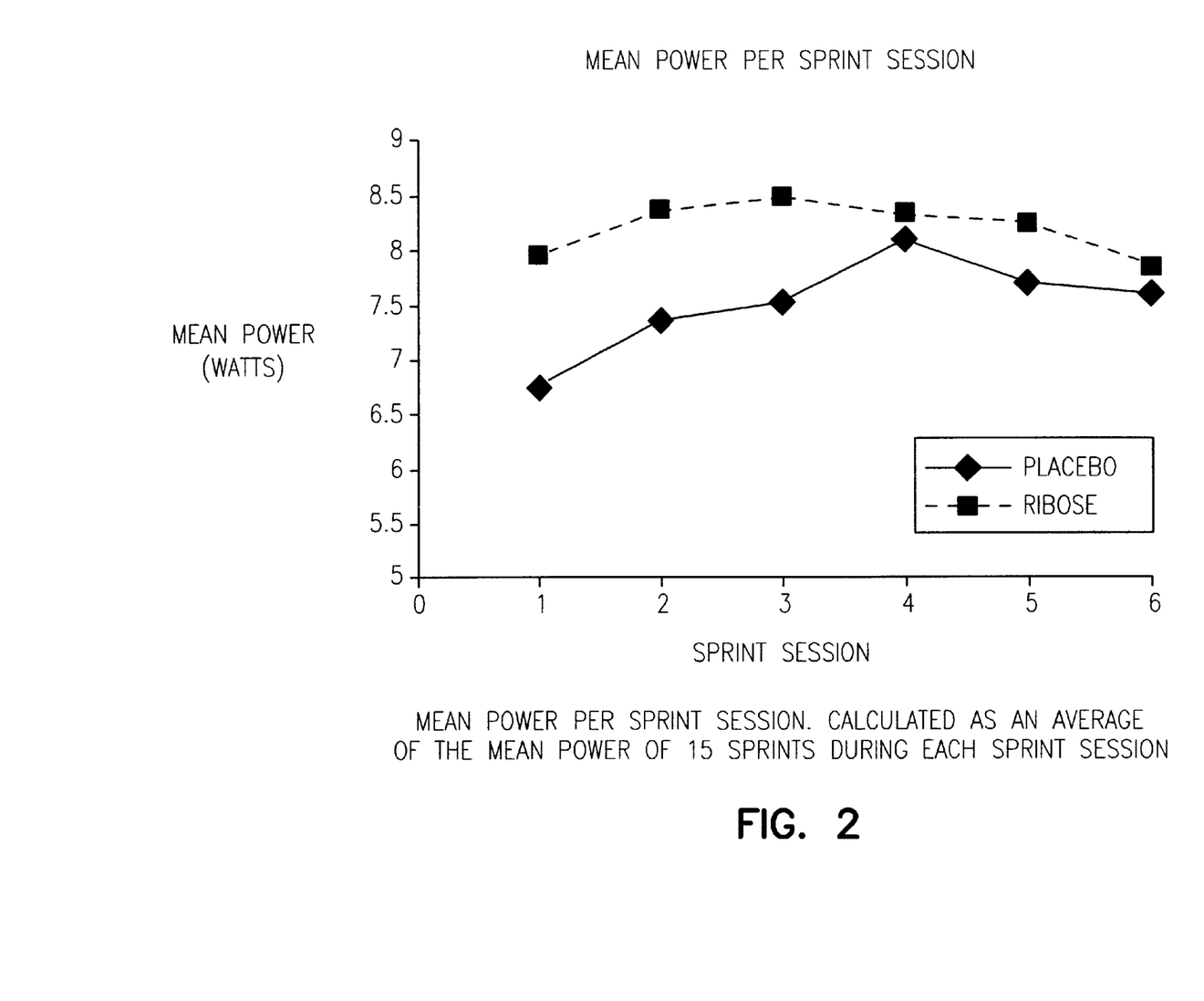
FIG. 2 shows the mean power output per sprint session of normal adult humans, following administration of ribose or placebo, as measured on an exercycle.
Figure 3:
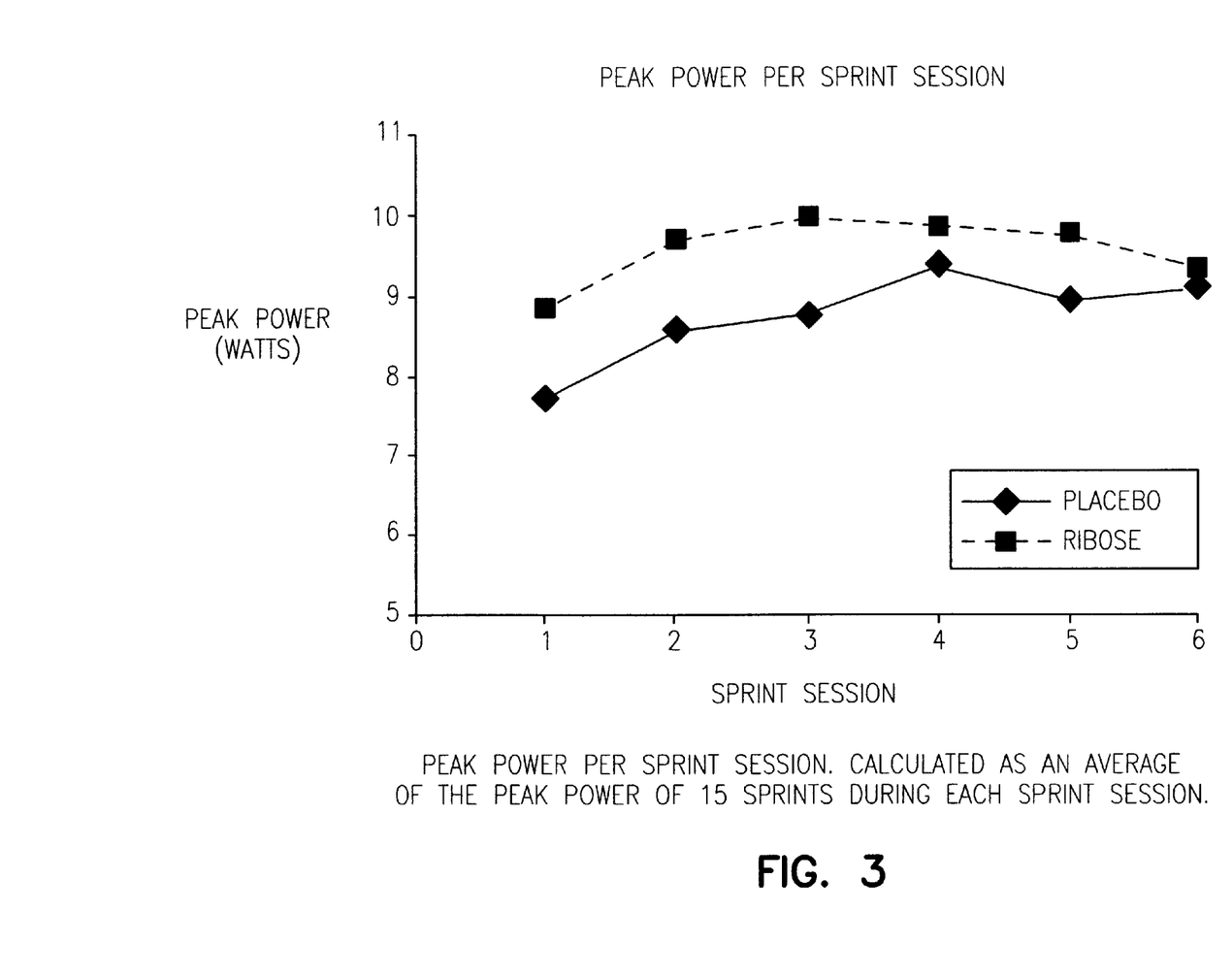
FIG. 3 shows the peak power output per sprint session of normal adult humans, following administration of ribose or placebo, as measured on an exercycle.

As can be seen from Tables II to IV and FIGS. 2 and 3, administration of ribose increased performance by 9%.

The improvement in performance is reflected in the ATP levels in the muscle biopsies. As shown in Table V, the subjects preloading with ribose for three days began the training phase with higher levels of ATP, which declined significantly more than that of the placebo group after the sprint bouts, indicating that ATP was being utilized more efficiently. Recovery of the ribose group at 48 hours was 82% of the initial level, compared to 78% in the placebo group.

TABLE V

Mean ATP Values (mmol/kg dw)

| Group | Pre | Post | Recovery | Recovery % of Pre | Change Pre-Post | Change Post-Rec |
|---|---|---|---|---|---|---|
| Placebo | 23.60 | 20.05 | 18.30 | 78% | −3.55 | −1.75 |
| Ribose | 25.33 | 13.90 | 20.80 | 82% | −11.43 | 6.90 |

EXAMPLE 3

Increased Athletic Performance and Reduced Fatigue in Athletes.

Following the studies of Example 2, in which it was shown that the levels of power output and muscle ATP could be increased above baseline in normal healthy subjects, this study was carried out using trained, conditioned athletes to determine whether the benefits seen in the normal healthy subject could be seen in conditioned athletes. Here the athletes were required to complete 15 sprint cycles versus 6 sprint cycles. Fatigue, that is, the inability to maintain a peak level of performance was measured.

Twenty-four male subjects, recreationally conditioned, ages 18–30, participated in this investigation. Prior to any testing the subjects were interviewed by a member of the investigation team. Potential subjects were excluded from the study if they were taking any nutritional supplements, if they smoked or had a history of metabolic, cardiac and/or pulmonary disease.

Approximately one week prior to the start of the investigation, subjects underwent a familiarization session to reduce the possibility of a learning effect and for equalization of the groups. Exercise was performed on a modified Monark bicycle ergometer. The exercise consisted of 15×10-second sprints, with a 50-second rest between each sprint. Thus, the 15 sprints were all performed in 15 minutes. Modifications to the ergometer allowed for accurate resistance to be applied to the flywheel. Resistance was calibrated using force transducers attached to the ends of the belt. The ergometer's resistance was et at 0.07 kg/kg body weight. For example, a 75 kg subject would exercise with a resistance of 4.9 kg.

Figure 4:
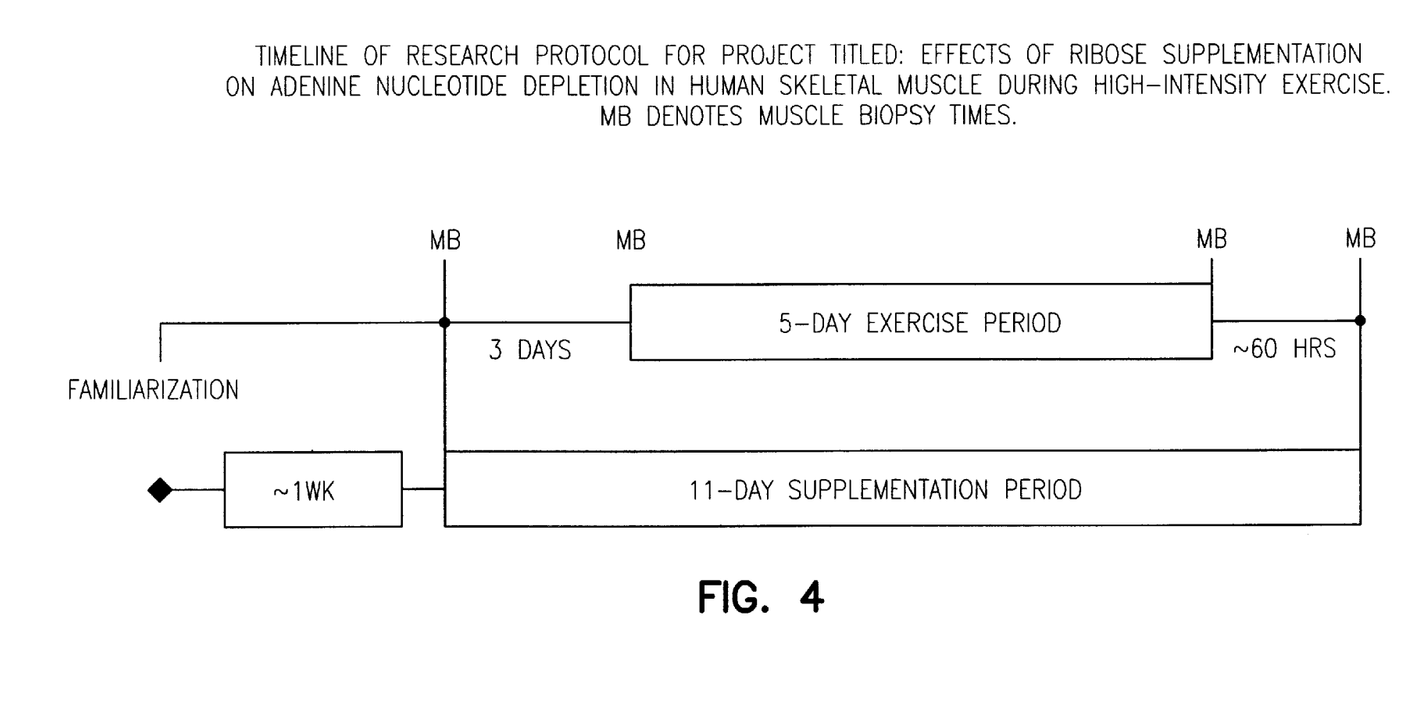
FIG. 4 shows the timeline for evaluating athletic performance.

The subjects were matched, based on their body weights and mean power values from the familiarization session, and randomly assigned to one of three groups. Following the familiarization session, supplementation was begun. One group consumed 20 g of placebo (glucose) supplementation each day, another group consumed 20 g of ribose supplementation each day and the third was given no supplement as a control for variations in performance and muscle data analysis. Supplements were supplied in 5 g packets, which the subjects consumed twice each, two packets in approximately 150 ml water. The two supplemented groups participated in the exercise protocol and completed four muscle biopsies. The control group participated in two exercise sessions separated by five days and two muscle biopsies. The time line for the supplementation and exercise periods is shown in FIG. 4.

The subjects in each of the two supplementation groups participated in a 5-day high intensity exercise procedure. The subjects started the exercise on day 3 of the 11-day supplementation period and continued through day eight. Exercise bouts were performed twice per day during the five-day exercise period. The sprinting protocol was identical to that in the familiarization session. At least six hours was permitted between each exercise session.

The Monark bicycle ergometer was interfaced with a personal computer that allowed for determination of power output and percent fatigue during each 10-second sprint. Data was collected at a rate of x hertz and averaged each second. Peak power, mean power and fatigue were determined for each 10-second sprint. The peak power was determined as the highest one second value. The mean power was determined as the average power over each 10-second sprint. Fatigue was determined as the percent decline from highest to lowest power values during each 10-second sprint.

Figure 5:
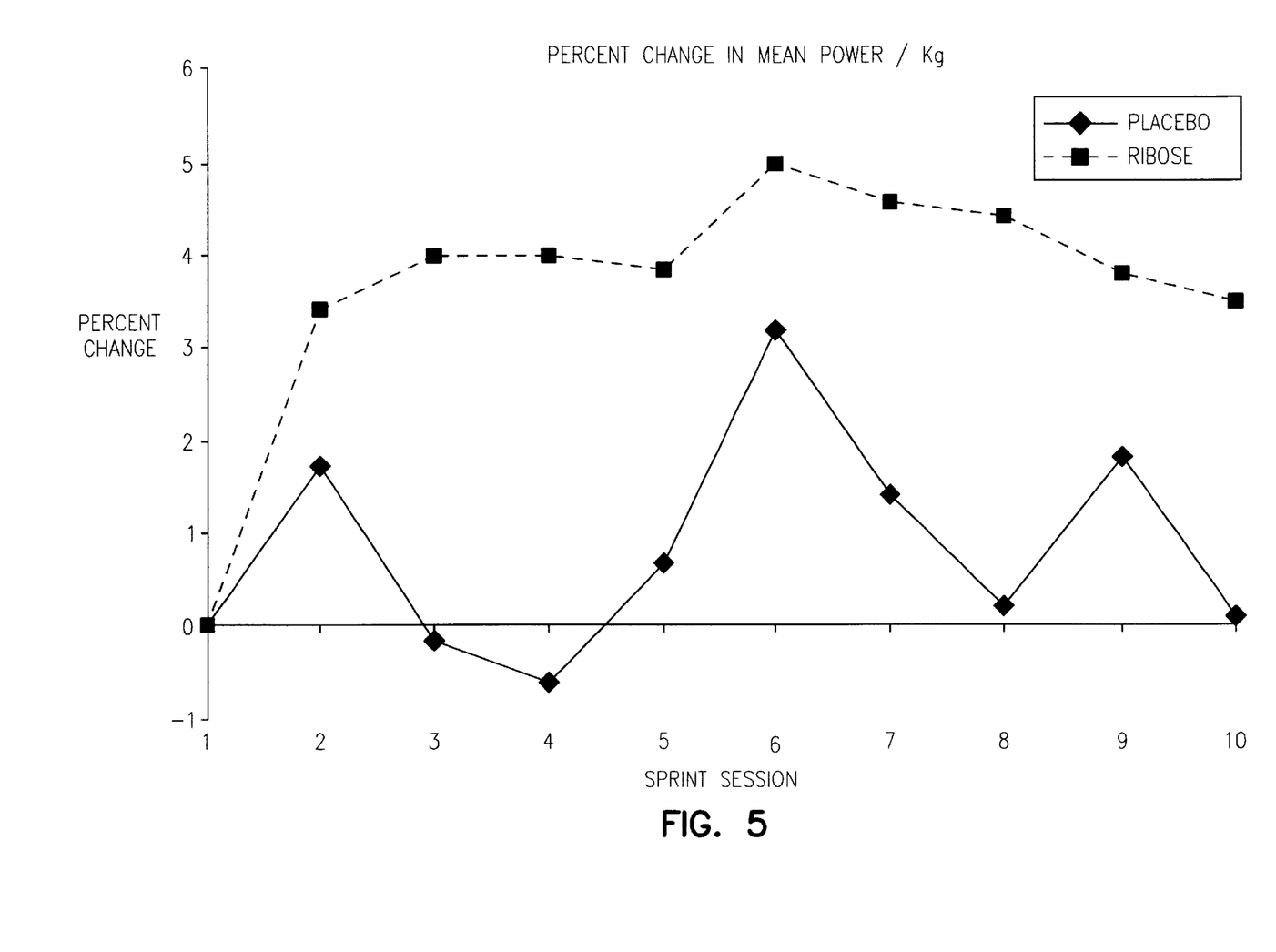
FIG. 5 shows the mean power output per sprint session of athletes, following administration of ribose or placebo, as measured on an exercycle.
Figure 6:
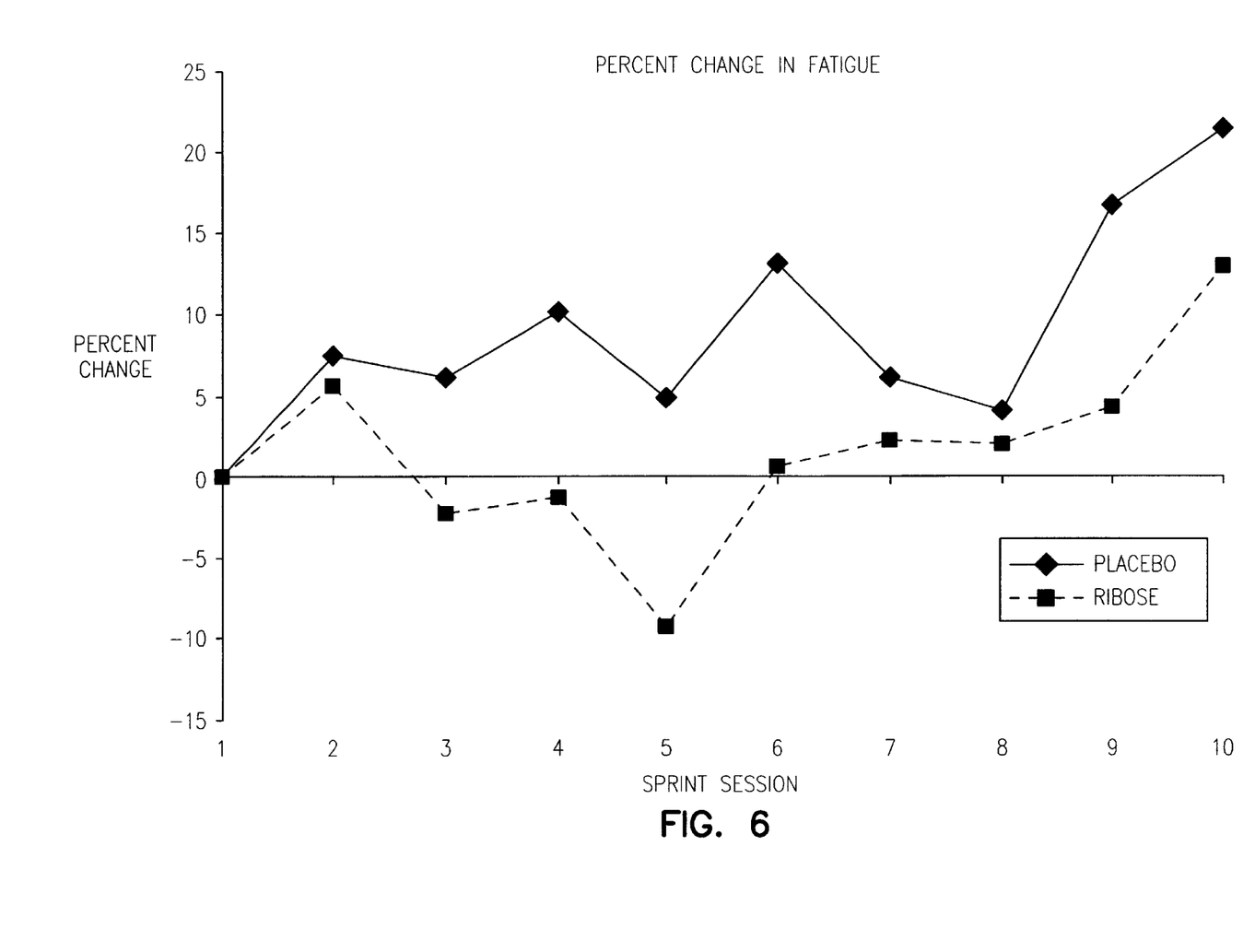
FIG. 6 shows the fatigue of athletes, following administration of ribose or placebo, as measured on an exercycle.

As is shown in FIG. 5, the ribose group increased its performance as measured by mean power output by about four percent over that of the placebo group and maintained the increase over the exercise period, in contrast to the placebo group, which showed a spike in mean power at six minutes, but declined to baseline at 10 minutes. FIG. 6 shows the percent change in fatigue. The ribose group was able to maintain an even performance, right up to the final sprint.

Four muscle biopsies were obtained from each subject in the two supplemented groups at the time indicated by MB on the time line of FIG. 4. As shown, the first biopsy was obtained prior to supplementation; the second was obtained immediately prior to the start of the exercise protocol and the third immediately following the final sprint on the fifth day of the exercise phase (eighth day of supplementation). The final biopsy was performed about 60 hours following the last training session (day 11 of supplementation). The two biopsies from the control group were obtained using the same 11-day schedule with the first biopsy taken on day one and the second on day 11.

Biopsies were taken from the vastus lateralis muscle using suction to aid in the collection of the sample. For this procedure, the area of the thigh to be biopsied was shaved and cleaned with an antiseptic. Then a small areas the muscle was numbed with 1.5 ml of lidocaine that also contained 1% epinephrine. The epinephrine cased a constriction of the blood vessels to reduce the bleeding at the biopsy site. After a five-minute period, a small incision (approximately one cm) was made with a #11 scalpel blade down through the fascia of the muscle. The biopsy needle was then inserted into the muscle and suction was applied via a small tube attached to the base of the needle on one end a 150 ml syringe on the other end., a small piece of muscle was then clipped off and the needle withdrawn. The sample was quickly frozen (within 10 seconds) to −120° C. and stored in liquid nitrogen. a small section (10–15 mg) of the first muscle sample was removed for fiber type identification. Briefly, the section was mounted on a number 2 cork in tragacanth gum with the fiber oriented vertically. The sample was then immersed in isopentane that was in the initial state of being frozen for approximately 20 seconds, and subsequently stored in liquid nitrogen until sectioning was performed.

Muscle samples stored at −20° C. were divided into section weighing between seven and 20 mg. One seven to 20 mg section of each muscle sample was extracted using perchloric acid (PCA) and analyzed for the following variables: ATP, ADP, AMP, IMP, hypoxanthine, xanthine, inosine, uric acid, adenosine and adenine. In addition, muscle ammonia was analyzed using an enzymatic/ spectrophotometric technique. For the extraction process, a seven to 20 mg section of each sample was placed in a tube containing 250 µl of 1 M PCA. The PCA was frozen to the temperature of liquid nitrogen, and the sample was allowed to come to a temperature of 0° C. for 30 minutes. The samples were then spun and 200 µl of the supernate was decanted and neutralized using 200 µl of 1 M potassium hydroxide and 50 µl of TEA. The samples were spun and 400 µl were decanted and stored at −80° until analysis was performed.

The muscle extracts were analyzed by modified reverse-phase high-performance liquid chromatography (HPLC) to determine the concentration of adenine nucleotides and degradation products. Separation was achieved using a 45-minute gradient elution with a Licorsorb 5 CH-18 (Phenomenex, Torrance, Calif.) column (250×4 mm). The mobile phases composition in buffer A was 150 mM ammonium phosphate, pH 5.80 and in buffer B was 78% ammonium phosphate, 20% methanol and 2% acetonitrile (pH 5.45). The following gradient schedule was applied during each run: 0–6 min, 100% a; 6–10 min. 75% a; 10–18 min, 0% a; 18–20 min. 0% a; 26–45 min, 100% a. Quantification of purines was achieved by comparison of values to standard curves derived for each variable.

During the exercise period, the total adenine nucleotides (AMP+ADP+ATP=TAN) decreased for both supplemented groups; the ribose showing a decrease of 26% while the placebo group decreased 38%, a statistical difference ($p<0.05$). 65 hours after the five day exercise period, the ribose group returned to pre-performance levels while the placebo group remained 23% below pre-performance levels ($p<0.05$). These data indicate that ribose supplementation partially attenuates the decrease in TAN following five days of high intensity exercise and is beneficial in the replenishment of TAN immediately following a high-intensity exercise bout, thus showing that the reduction of fatigue seen during the exercise bouts continued as quicker recovery of TAN to pre-performance levels in the days following the exercise.

EXAMPLE 4

The Effects of Ribose Supplementation on Athletic Performance in Recreational Male Bodybuilders.

Bodybuilders undergo rigorous athletic performance in the course of enhancing muscle development. In this study, ribose was administered for four weeks, during which time the subjects participated in a heavy-resistance training program designed for muscle building.

Healthy, trained men were recruited from the student population of the University of Nebraska via posted advertisement and word of mouth. In order to participate in the study, subjects had to meet the following inclusion criteria: a) 18–35 years of age; b) in good health by self-reporting (free from diabetes, cancer, heart disease, or orthopedic impairment); not currently taking a dietary supplement that contained colostrum; d) already performing resistance-training at least three times per week for the last six months. Informed consent was obtained from each subject and the experimental procedures were approved by the institutional review board of the university.

The study was double-blinded and placebo-controlled. Subjects were randomly assigned to a placebo (glucose) or ribose group. Subjects orally ingested 10 grams daily of ribose or placebo for four weeks. Subjects were instructed to consume 5 grams of supplement 30–60 minutes prior to training and 30–60 minutes post-training. All subjects were instructed not to change their dietary habits. Twenty-four hour dietary recalls were obtained from all subjects on a random day during the first and last week of the study. Energy and macronutrient intake were analyzed via computerized analyses (Nutribase '98, Phoenix, Ariz.).

Table VI shows the split-routine, periodized resistance training program. Subjects kept a training log to ensure compliance with the training regimen.

TABLE VI

| Training Regimen | | |
|---|---|---|
| Chest, Shoulders, Triceps Day 1 Choose 6 exercises | Legs Day 2 Choose 6 exercises | Back, Biceps Day 3 Choose 6 exercises |
| Bench press*# Incline bench press Dumbbell military press Front raises Cable crossovers Pec deck Dumbbell bench press Tricep kickbacks Lateral raises | Squats# Calf raises Leg extensions Leg curls Leg press Dumbbell lunges | Lat pull-downs# Dumbbell rows Seated rows Hammer curls Reverse grip pulldowns Shoulder shrugs Dumbbell bicep curls |

*Subjects will perform the bench press exercise to momentary muscle failure during the last set.

Each subject was skilled in the bench press exercise. After three-warm-up sets, subjects were instructed to perform a one-repetition maximum (1-RM) on the supine free-weight bench press. In addition, the maximal number of full repetitions of 100% body weight was assessed for 10 consecutive sets (one minute rest between sets). During the test, subjects had their feet fully planted on the floor, their hips and scapula maintained contact with the bench at all times, and a slight lumbar lordosis was allowed. Repetitions were performed such that the concentric phase was performed as quickly as possible and the eccentric phase was performed with a controlled descent. Hand position was slightly greater than shoulder width. A graduate student in exercise physiology performed each test and determined if a repetition was performed correctly.

The ribose group experienced a significant pre-post increase (+29.8% ribose vs. +7.42% placebo) in the number of total repetitions performed to muscular failure for the ten sets ($p=0.046$).

EXAMPLE 4

Increased Stamina and Feeling of Well-being in Normal, Untrained Subjects.

D-ribose, given immediately before and during exercise, can provide a benefit to those subjects who have not been previously trained. Four healthy, normal male volunteers will be tested for sprint power output on an exercycle, as for Example 2 above. Each subject will serve as his own control. Between the sprint bouts, the subjects will cycle slowly and continuously. Total test time will be one hour, with four sprint bouts during the test. Following the initial baseline test and following each sprint bout, the subjects will be given 5 grams of D-ribose in 200 ml. of water or a similar tasting placebo (glucose). Sprint power output will be tested 15 minutes after each ingesting of the test solutions. Each subject will undergo two sessions, one week apart, one with ribose and one with placebo, in randomized order. The placebo will be sweetened with glucose in order to be indistinguishable from the ribose solution. It is expected that the subjects will show higher power output after ribose administration following sustained mild exercise than they showed after placebo administration. It is further expected that the subjects will have a subjectively higher feeling of well being.

EXAMPLE 5

Improved Performance in the Horse.

Ribose supplementation has been tested in thoroughbred and trotter racehorses. Ribose has been distributed to several stables. It has been found that a maintenance dose of 20–27 g daily, added to normal feed without other supplementation, has increased several of the horses' performances to the extent of shaving seconds off their lifetime marks. Best results have been found by increasing the dose on the day of a race to 27–30 g given one dose prior to the race and the other dose after the race. For convenience, the maintenance dose is mixed dry into the feed or sprinkled on top of the hay, while the before-the-race dose can be given mixed in a minimal amount (~250 ml) of water. Results have been seen in an improvement in the horses' finishing positions in the race and in many cases an improvement in time at a particular track.

One race horse, "A Pirates Defense," that was nearly ready to be put out to pasture, was fed ribose three days before a race and on the day of the race at 27 g twice a day. This horse had never before been a high performer in its entire career. The day of the race following the ribose administration the horse placed first, pulling away from the pack half way through the race. The odds posted that day against the horse were 45;1.

Other racehorse trainers have used as much ribose at 100 g per dose without ill effects.

Greyhound dogs also race in meets that are similar to horse races. These dogs will benefit from a similar regimen of ribose administration, adjusted to their lower body weight of 65–70 pounds. The preferred dosage for a racing dog is about 0.15 to 4 g per dose, administered twice daily as a maintenance dose, with about 1 g being administered before and after each race.

EXAMPLE 6

Self Administration of Ribose.

Patients with chronic illnesses, including but not limited to coronary artery disease, AIDS, intermittent claudication, tuberculosis and chronic fatigue syndrome, that are characterized by low energy levels, and even those subjects free of overt disease but having low energy due to advanced age, trauma, burns, and recovery from illness or surgery, are benefitted by being able to raise their energy levels without continual medical intervention. Many individuals with relatively stable disease live a day to day existence by conforming to an altered life style, coupled with pharmaceutical supplementation. Often, such subjects are inhibited from undertaking a regimen of moderate physical activity from fear of inducing unpleasant effects, such as angina, breathlessness, muscle soreness, cramping or a feeling of exhaustion. Such avoidance lowers the quality of life of the subject and engenders an ever-present background anxiety. In addition, the benefits of moderate exercise, which include improved digestion, sleep and a more relaxed and positive state of mind, are denied to such subjects. Even subjects free of disease and considered healthy may be dissatisfied with their subjective feeling of energy level and well being.

An example of a subject having no overt disease who benefitted from self-administered ribose is a fifty-five year old male. He had adhered to a strict weekly exercise regimen most of his life until sustaining a systemic bacterial infection, which required admission to the intensive care unit for one month and rehabilitation for an additional month. His cardiovascular and pulmonary systems were predominantly affected during and following his illness and function had not recovered to its previous levels, or to his satisfaction, after one year.

Following convalescence, he has attempted to resume an exercise regimen, which involves running on a treadmill four days a week and lifting weights for two days a week. The runs were restricted to short intervals. Following the daily exercises, he has continuously experienced fatigue to the point of exhaustion and has required frequent naps. The patient began self-administering oral D-ribose at two doses per day, 4–5 grams per dose. Within seven days, he testified that his "pep" and exercise tolerance has increased. For the first time since his illness, he is able to run as long as 30 minutes on the treadmill. He still experiences a degree of fatigue, but has been able to discontinue the naps after exercise. He continues on the daily oral doses of ribose, along with his scheduled exercises and feels a continuing improvement in his energy level after four weeks of ribose administration. He has experienced no adverse effects from the ribose.

All publications and patents cited herein are incorporated by reference as though fully set forth. This invention has been described with respect to various specific and preferred embodiments. However, it should be understood that many variations or modifications may be made while remaining within the spirit and scope of the invention.

We claim:

1. A method for increasing the athletic performance which comprises the oral administration of an amount of a pentose to said mammal, said amount being effective to increase the athletic performance of said mammal.

2. The method according to claim 1 wherein the pentose is ribose.

3. The method according to claim 1 wherein the mammal is a human.

4. The method according to claim 1 wherein the mammal is a horse.

5. A composition to be administered to increase athletic performance and reduce fatigue in mammals which comprises an effective amount of a pentose.

6. The composition according to claim 5 wherein the pentose is ribose.

7. The composition according to claim 5 which further comprises a stimulant, an energy pathway subtrate or intermediate, creatine, carnitine, forskohlin, ipriflavone or mixtures thereof.

8. A unit dosage form comprising about 0.1 to 200 gm pentose in combination with a pharmaceutically acceptable vehicle, adapted for oral ingestion.

9. The unit dosage form of claim 8, wherein the pentose is ribose.

10. The unit dosage form of claim 8 wherein the vehicle is a liquid.

11. The unit dosage form of claim 10 wherein the liquid is an aqueous liquid.

12. The unit dosage form of claim 8 wherein the vehicle is a solid or semi-solid edible vehicle.

13. A method for reducing the fatigue associated with an athletic performance of a mammal which comprises the oral administration of an amount of ribose to said mammal, said amount being effective to reduce the fatigue experienced by said mammal due to said athletic performance.

14. A method for decreasing the recovery time to pre-performance levels of total adenine nucletides of a mammal following depletion of total adenine nucleotides due to athletic performance comprising the oral administration of an amount of ribose to said mammal, said amount being effective to decrease the recovery time to pre-performance levels of total adenine nucleotides.

15. A method for increasing the athletic performance during exercise in a human subjected to said exercise which comprises administering between 3 and 30 g of ribose daily to said human.

16. A method for increasing the athletic performance of a horse which comprises administering between 30 and 300 g of ribose daily to said horse.

17. A method for increasing the athletic performance of a racing dog which comprises administering between 1.0 and 8 g of ribose daily to said racing dog.

* * * * *